(12) United States Patent
Lipow et al.

(10) Patent No.: US 9,498,298 B2
(45) Date of Patent: Nov. 22, 2016

(54) RING FORM SURGICAL EFFECTOR

(76) Inventors: Kenneth I. Lipow, Bridgeport, CT (US); Gary Zimmerman, Wesport, CT (US)

( * ) Notice: Subject to any disclaimer, the term of this patent is extended or adjusted under 35 U.S.C. 154(b) by 1578 days.

(21) Appl. No.: 12/799,427

(22) Filed: Apr. 23, 2010

(65) Prior Publication Data
US 2011/0264078 A1    Oct. 27, 2011

(51) Int. Cl.
| | | |
|---|---|---|
| *A61B 17/00* | (2006.01) | |
| *A61B 19/00* | (2006.01) | |
| *A61B 18/20* | (2006.01) | |
| *A61B 17/34* | (2006.01) | |

(52) U.S. Cl.
CPC ............... *A61B 90/11* (2016.02); *A61B 90/50* (2016.02); *A61B 18/20* (2013.01); *A61B 34/25* (2016.02); *A61B 90/30* (2016.02); *A61B 2017/00221* (2013.01); *A61B 2017/00477* (2013.01); *A61B 2017/3409* (2013.01); *A61B 2090/378* (2016.02)

(58) Field of Classification Search
CPC ............................... A61B 90/11; A61B 90/50
USPC .................... 606/130, 129, 1; 601/1
See application file for complete search history.

(56) References Cited

U.S. PATENT DOCUMENTS

| 4,887,599 A | * | 12/1989 | Muller ........................... 606/180 |
|---|---|---|---|
| 5,342,352 A | * | 8/1994 | Franken et al. .................. 606/9 |
| 8,137,279 B2 | * | 3/2012 | Taylor et al. .................. 600/459 |
| 2001/0013764 A1 | | 8/2001 | Blumenkranz et al. |
| 2002/0019641 A1 | | 2/2002 | Truwit |
| 2004/0243147 A1 | * | 12/2004 | Lipow ........................... 606/130 |
| 2005/0033337 A1 | * | 2/2005 | Muir et al. ..................... 606/167 |
| 2008/0097187 A1 | | 4/2008 | Gielen et al. |
| 2010/0152749 A1 | * | 6/2010 | von Pechmann et al. .... 606/130 |

* cited by examiner

*Primary Examiner* — Lynsey Crandall
*Assistant Examiner* — Sebastian X Lukjan
(74) *Attorney, Agent, or Firm* — DeLio, Peterson & Curcio, LLC; Kelly M. Nowak (57) ABSTRACT

The present invention is a surgical ring form structure including a surgical ring where the surgical ring is a circular structure adapted to receive a surgical implement rigidly affixable with respect to the surgical patient and the surgical ring, an electrical circuit allowing the surgical implement to be electrically communicable with a remote controller, a surgical implement as an effector unit, an effector unit configurable to operate a laser, ultrasound device, lights, camera, and other imaging and monitoring devices capable of two-dimensional and three-dimensional capture, a circular rail respective to the surgical ring whereupon controlled motion of the surgical implement or effector unit is provided, remote display and interfacing capabilities with the surgical implements, remote controlling interfaces for controlled motion of the surgical implements with respect to the surgical ring and the patient, and an electrical circuit having contacts extending along the periphery of the surgical ring.

19 Claims, 7 Drawing Sheets

RING FORM SURGICAL EFFECTOR

The present invention claims priority from U.S. Provisional Patent Application Ser. No. 60/214,396, the contents of which are incorporated herein in their entirety by reference thereto.

BACKGROUND

The present invention relates to the field of remote controlled and computer assisted surgery, and more specifically to equipment and methods for remote controlled and computer assisted microsurgery.

As shown in U.S. Pat. No. 5,943,914 to Morimoto et al., "Master/slave" equipment for performing surgical procedures are known in which a surgeon's hand input is converted into a movement by a surgical effector, which while frequently referred to as a robot is more accurately a remotely controlled surgical effector, as it performs very limited motions which are fully automated. The conversion of the hand motions of the surgeon into movements of a surgical implement through such an effector is particularly useful for motion scaling wherein a larger motion in millimeters or centimeters by the surgeon's input is scaled into a smaller micron movement.

As described in Applicant's previously filed patent applications U.S. patent application Ser. Nos. 10/738,359, 11/249,041, 11/255,899 and issued U.S. Pat. No. 7,198,630, the contents of which are incorporated herein in their entirety by reference thereto, control systems for implementing such effectors were limited with respect to the feedback provided to the operators of such devices. Notwithstanding, the form of the actual effector which could be utilized to implement the improved control system likewise was limited in its utility, primarily as a result of the structure utilized to position and utilize surgical implements within the surgical field.

Manual surgical procedures, or non-computer assisted surgeries, are subject to human limitations. In manual surgical procedures, surgeons face difficulty in properly judging the three-dimensional geometries of objects encountered during a procedure, acquiring points with precision with surgical instruments, grasping and manipulating tissue over time, maintaining cognitive focus upon exertion of personal dexterity, recalling precise self motion for greater than a thirty-second period, maintaining motor performance over time, maintaining stillness during procedure, maintaining track of surgical field materials, multitasking when concentrating, and properly feeling tissue through instrumentation.

Likewise, the operating room environment in manual surgical procedures poses several major limitations with regards to stabilizing the position of the patient and the physically invasive nature of analog surgical microscopes. Surgical microscopes are, typically, large and bulky devices weighing up to 500 pounds. Such devices confine and obscure the line of sight view of the operating field to the surgeon and, thereby, limit the effectiveness of the individual surgeon. An example of such a device is the NC-4 Operating Microscope manufactured by Carl Zeiss. Further difficulty is created by use of such analog surgical microscopes by the fact that they must be removed from the patient and the operating room must be rearranged, creating a serious risk of loss of sterility.

Current systems using robotic instruments, such as the DaVinci System manufactured by Intuitive Surgical, can not be used for open surgery, or are limited to specific procedures, such as laparoscopic prostate surgery or gynecologic oncology procedures. Further, such systems require specialized training and certification. As discussed herein, the present invention provides a solution to the above-described challenges in the prior art.

SUMMARY OF THE INVENTION

In accordance with the first aspect of the invention, a surgical ring form structure is provided, wherein the surgical ring form comprises a circular structure adapted to receive a surgical implement wherein the surgical instrument is rigidly affixable with respect to a surgical patient, and further comprises an electrical circuit allowing the surgical instrument to be electrically communicable with a remote controller. By way of non-limiting example, the surgical implement is an effector unit configurable to operate a laser, an ultrasound device, lights, cameras, or other surgical implements capable of a surgical, imaging, three-dimensional imaging, mapping, or other relevant function and may further have remote control and observation capabilities. The effector unit may be capable of controlled motion with regards to a circular rail respective to the ring form and may further be remotely controllable via a remote display and interface system where communication is provided by an electrical circuit, the electrical circuit may further extend around the periphery of the ring form and/or comprise a power signal through implementation of an electrical contact. The electrical circuit may further comprise a plurality of electrical paths wherein such electrical paths form a signal bus for allowing a plurality of surgical implements to be concurrently in communication with a remote controller via the signal bus. A plurality of positioning systems may be provided to position the effector unit with respect to the circular rail and the surgical instrumentalities active thereupon. Alternatively, the effector unit may be a configurable stationary fixture upon the circular rail.

DETAILED DESCRIPTION OF THE INVENTION

The present invention is an expansion on the passive surgical rings presently on the market. Passive surgical rings operate to only provide an arm rest or passive holding mechanisms for surgical instrumentalities. The present invention discloses a powered interactive platform by which an operator may remotely operate instrumentalities via an operator interface control system. In comparison to the prior art use of analog surgical microscopes, the present invention discloses a system which may be light-weight and portable.

The preferred embodiment of the present invention is directed generally to the area of neurosurgery, but may be easily adapted to areas including, but not limited to, retinal surgery, vascular surgery, neonatal surgery, prenatal surgery, pediatric surgery, gynecologic oncology surgery, and plastic surgery.

Figure 1:
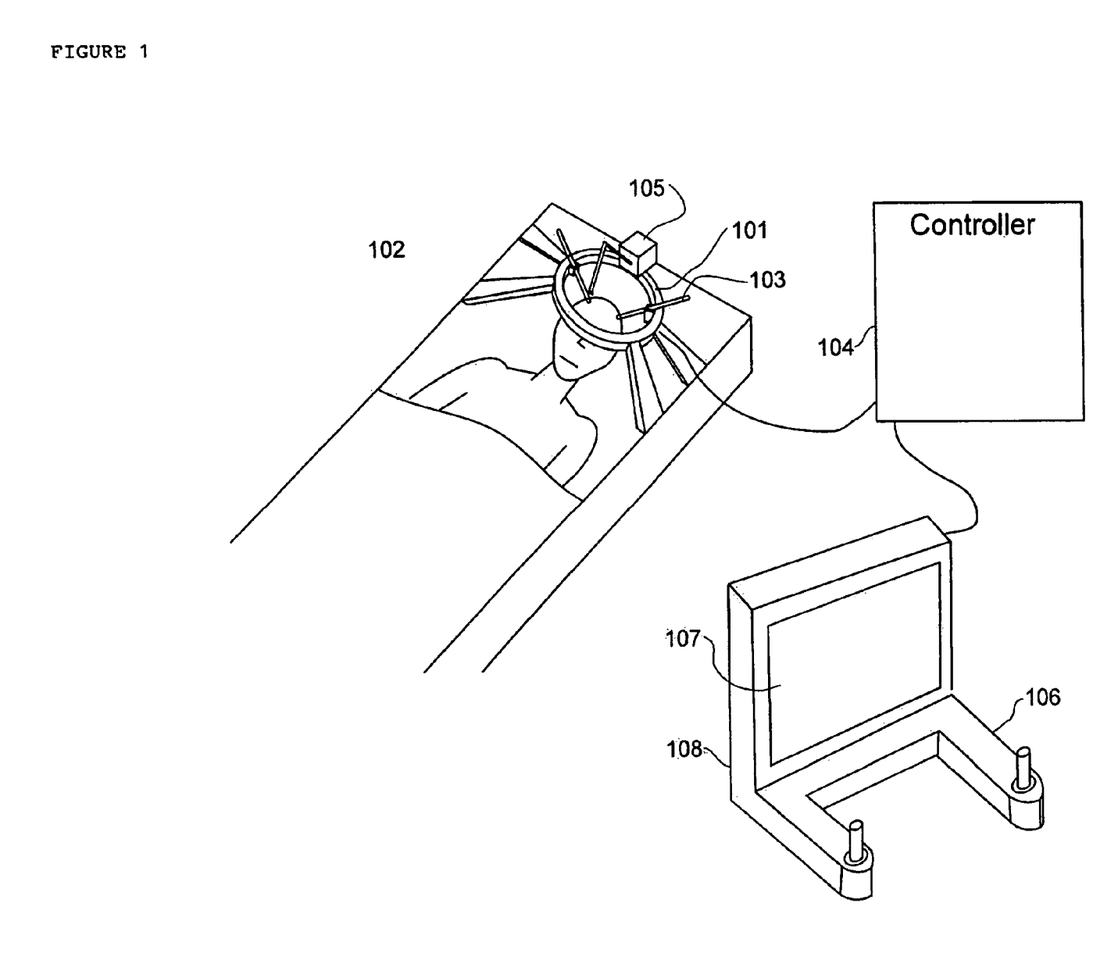
FIG. 1 illustrates a ring form surgical robot according to the present invention, wherein multiple effector units are engaged to the ring form.

As shown in FIG. 1, the present ring structure surgical effector is generally formed from one or more rings 101, which can be fixed in position with respect to a surgical field 102, similar to the Budde Halo system manufactured by Integra LifeSciences Corp. A large distinction exists between such a halo system and the present invention, in that the present invention implements active components, rather than simply providing a passive structure for resting a surgeon's arms on or for attaching passive elements to.

The ring structure surgical effector may utilize one or more circular elements, to function as guides, mechanisms for translation of active units 103 around the ring structure, and electronic communication between an active element 103 and controllers 104 located either within the ring structure, or located at a distance from the ring controller.

Mounted to the ring structure may be one or more different types of modular effector units 105. Each effector unit 105 may have one or more moveable arms for implementing procedures. The moveable arms may be provided with quick change tool holders, such that various surgical implements can be rapidly engaged to or removed from the moveable arm.

Figure 2:
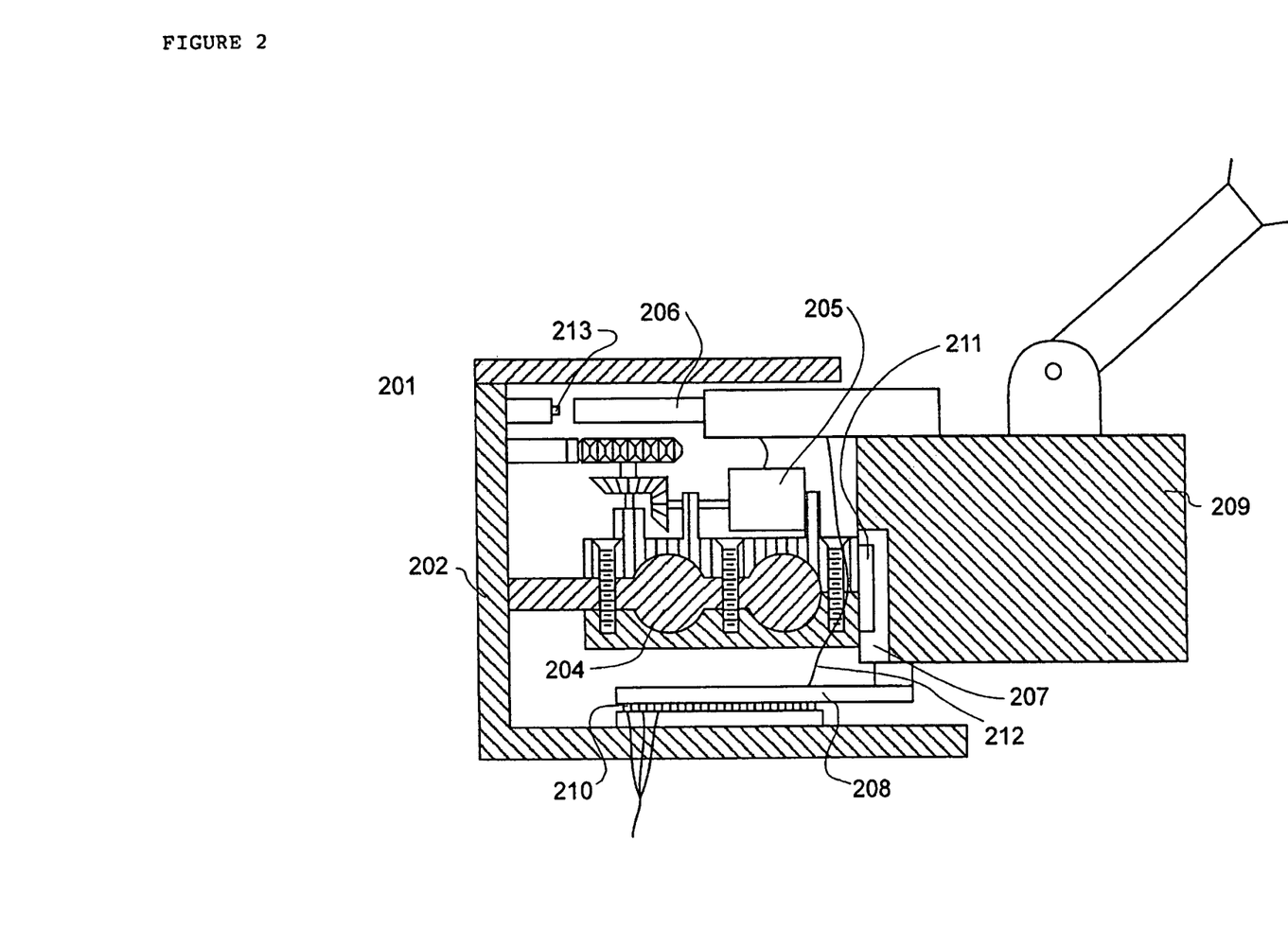
FIG. 2 illustrates an embodiment of the ring form surgical robot in cross section, illustrating the connections between the ring form and an effector unit.

One possible implementation of the ring form effector 201 is shown in cross section in FIG. 2. The ring form in cross section uses an outer case 202, to which a circular slide 203 is affixed. The circular slide 203 utilizes parallel rails 204 which may be generally circular in cross section. The rails 204 may be connected to the outer periphery of the ring form. In an alternative embodiment, the ring form may take another shape, geometric (circle, oval, rectangle, etc.) or organic, as required by the surgical field within which the present invention operates.

The ring form 201 may also be provided with a gear surface that can be engaged by a drive gear 205 on an effector mount, to allow the effector mount to self traverse around the periphery of the ring form. A position sensor 206 may additionally be implemented, such that the absolute position of the effector mount 207 with respect to the ring form 201 can be determined. In an alternative embodiment, the effector mount 207 may be manually placed at a fixed location by an operator, wherein its position may be adjusted as required.

The ring form 201 may additionally be provided with slip rings 208, or any other suitable means, to allow electrical contact between an effector mount and the ring form 201 (and from there to an effector controller) such that remote control of the effector mount 207 and an effector unit 209 attached to the effector mount may be accomplished. The slip rings 208 may provide a plurality of electrical paths 210, such that a data bus may be created by the contacts, such that the same slip ring 208 connections may be used to communicate with multiple effector mounts.

The ring form 201 and related structures may include a means for sterilization, including a heating element or gas-based sterilization method or any other suitable means therefor.

A cover may be provided over the internals of the ring form 201, to reduce interferences between objects in the surgical field and the ring form effector 209. The cover may additionally reduce the amount of extraneous matter which can enter into and/or interfere with the internals of the ring form effector 201, which could otherwise occur should the internals be open to the surgical field Effector units 209 may be connected to the ring form effector 201 through the effector mounts 207. The effector mounts 207 may have a structural adapter 211 to allow effector units 209 to be rapidly engaged to or removed from an effector mount 207, such that if necessary, effector units 209 can be swapped during a procedure, such as to replace one type of effector unit 209 with a different type of effector unit 209, or to replace a malfunctioning effector unit 209. The electronic communications path between the ring form effector 201 and the effector mount 207 or mounts can be further extended to the effector unit 209 itself, either by a connector engaged concurrently with the structural engagement 211 between the effector unit 209 and an effector mount 207, or via a separate cable.

The effector mount 207 may utilize a sliding bearing for engaging the circular rail 204 to provide smooth movement of the effector mount 207 relative to ring form effector 201 to allow effector mounts 207 to be repositioned within a surgical field. The sliding bearing may preferably comprise a separable shell 213 to allow the effector mount 207 to be removed from ring form effector 201, such as for cleaning or maintenance. The effector mount 207 may be provided with a plurality of contacts to allow the effector mount 207 to electrically contact the slip rings 208. The effector mount 207 may additionally be provided with a position sensor, to allow determination of the position of the effector mount 207 with respect to the ring form effector 201.

Figure 3:
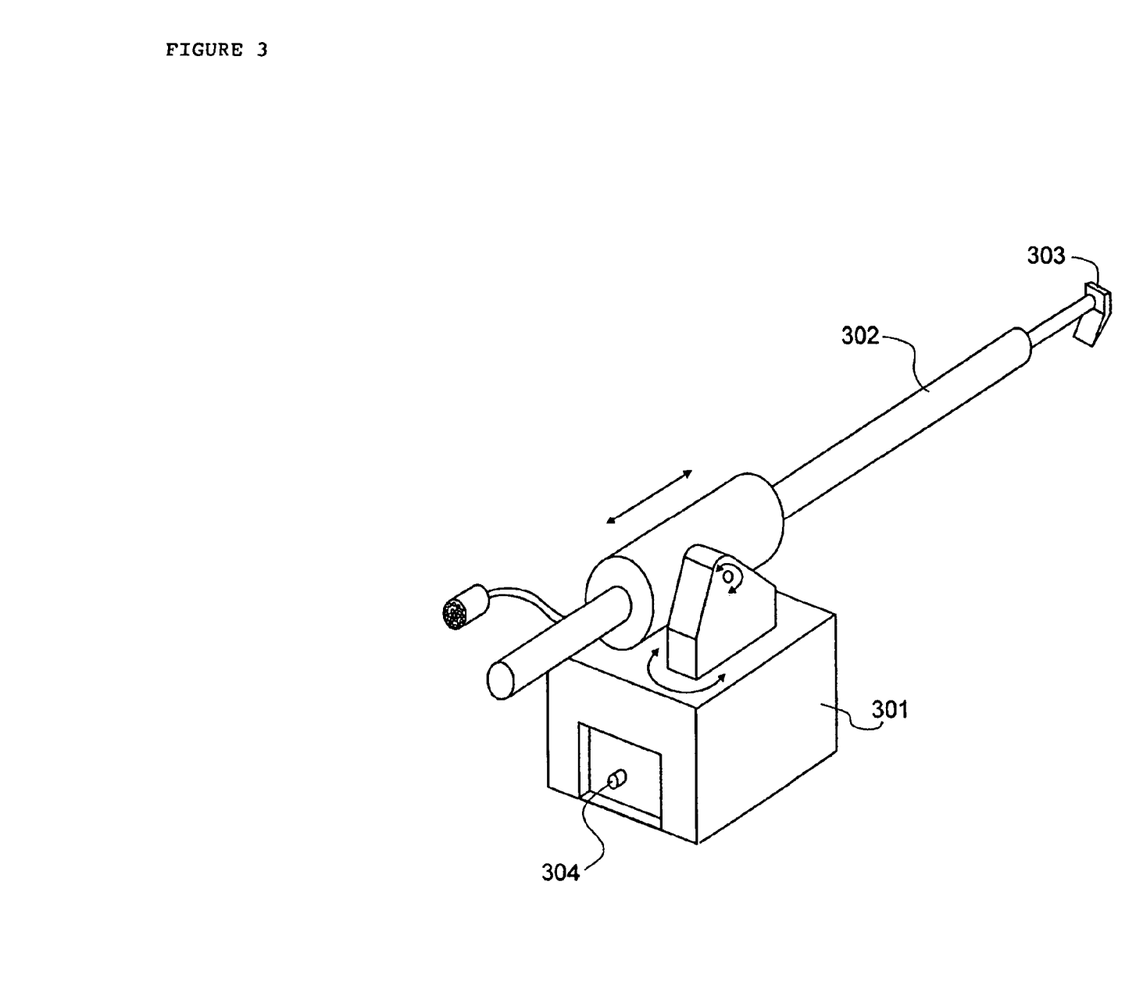
FIG. 3 illustrates a potential effector unit for accomplishing a surgical procedure in accordance with the present invention.

As shown in FIG. 3, effector units 301 may be tailored for specific tasks, such as use as a retractor 302. A retractor application may have an extendable arm 303 for extending into the surgical field, as well as a rotational degree of motion to allow the arm to be positioned within the field. The arm 303 thus would be moveable in extension, rotation, and traverse around the ring form effector, such that it would be able to be positioned within the surgical field as required. An additional degree of freedom could be provided to allow additional freedom with respect to positioning a retractor 302 feature within a surgical field.

As shown in the figure, the retractor effector unit 302 could be provided with a notch 304 for receiving an attachment feature from an effector mount 207, thus allowing the effector unit 301 to be quickly engaged to or removed from the effector mount 207. The receiver 304 may be provided with a positive retention capability, such as a pin which extends from the effector unit 301 or the effector mount 207, to lock the effector unit 301 to the effector mount 207.

Figure 4:
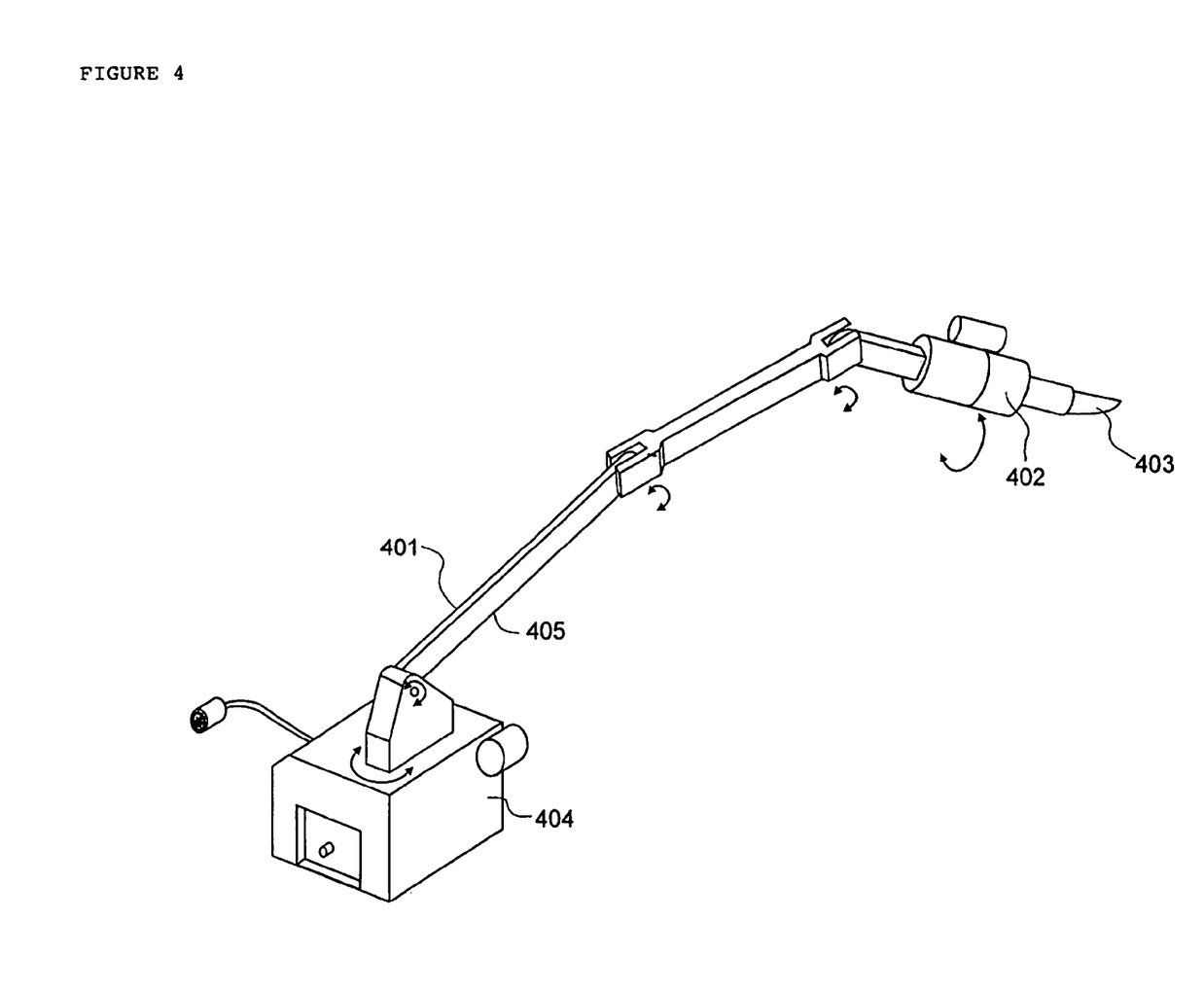
FIG. 4 illustrates a potential effector unit for accomplishing a surgical procedure in accordance with the present invention, in particular to assist with the retraction of tissue during such a procedure.

As shown in FIG. 4, the effector units 404 may alternately or additionally be provided with a different form of arm 401, to allow different motion within the surgical field. In FIG. 4, the arm 401 is articulated at approximately mid span, with a mid-span rotational degree of freedom. A quick change tool holder 402 may be provided at the end of the arm to allow engagement of a surgical implement 403, such as a scalpel, to be engaged to the arm. A rotational degree of freedom may be provided at the tool holder 402 to allow the tool 403 to be rotated within the surgical field, as well as at the wrist formed between the tool holder and the arm to allow orientation of the tool holder with respect to the arm. The arm 401 may further include sensor instrumentation to allow the position of the arm 401 and/or surgical implement on the end of the arm to be determined, and provided as input to a controller. Force measurement systems, such as load cells, may also be included such that force reflectance from a surgical implement can be reported to a system controller.

The engagement between the arm 401 and the effector unit 404 may be provided with two degrees of freedom, such that the inner arm 405 section may be oriented relative to the effector unit 404, such that the combination of the tool holder 402 rotation, wrist rotation, mid-span rotation, inner arm rotation, and inner arm yaw allow fine positioning and orientation of the tool 403 within the surgical field.

Multiple ring form effectors may be stacked to allow a greater number of effector units to be moved within a surgical field. In the event that stacked ring form effectors are utilized, care must be used to obviate interference between surgical implements and associated effector units within the surgical field. Such care may be implemented in a controller which predicts position of the surgical implements and effector units based on position and motion within the surgical field. In an alternative embodiment, the multiple rings are tiered such that noninvasive instrumentalities are positioned on the effector mounts coupled to the outer tier, whereas invasive instrumentalities are positioned on an inner tier closer to the operational field and target structure, or any desirable combination thereof.

The effector units may be provided with sensors to determine both orientation of the various joints, as well as force being applied to a surgical implement associated with an effector unit. The determination of force and position allows these values to be provided as feedback to both a controller system, such as that described in Applicant's earlier applications, as well as to an operator of the unit.

The effector units may additionally be provided with cameras or other visualization devices to provide an operator with visual feedback of the surgical field. Such cameras may be independent to a previously mounted instrumentality or be located with a field view, or along a surgical implement axis, to provide the operator with a "tools eye view." Such cameras may utilize high definition sensor technologies. Illumination devices may further be provided via static or configurable stems coupled to the effector units to provide infrared, ultraviolet or other illumination within the surgical field.

Figure 6:
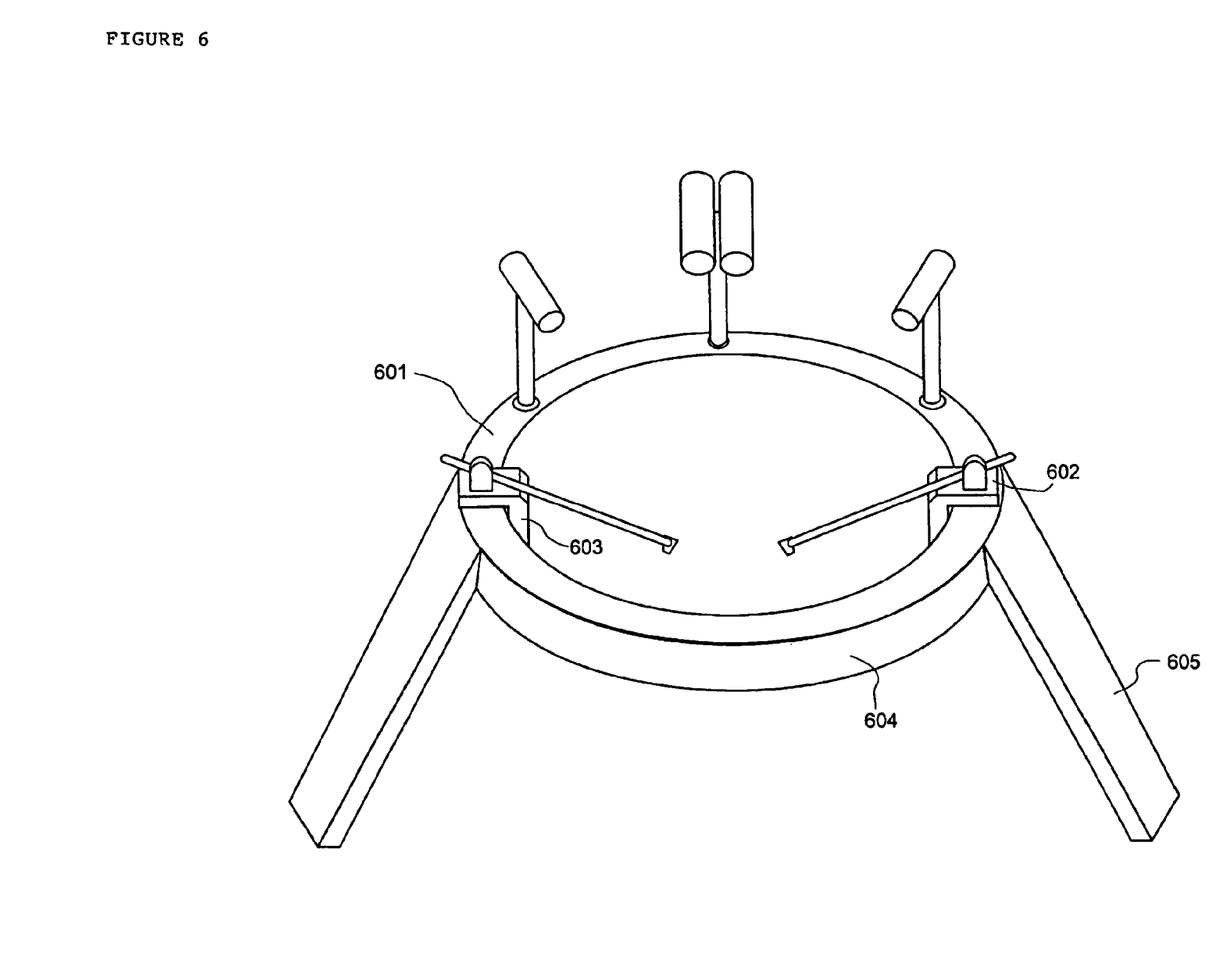
FIG. 6 illustrates a simplified embodiment of the present ring form, wherein the ring form does not provide for dynamic translation of surgical implements with respect to the circular ring form structure.

The effector units 601 may further be provided with therapeutic, diagnostic, surgical, mapping, imaging or sensing devices such as a surgical laser, an ultrasound probe, an interactive tissue monitor or other probe (tissue compression sensing, $PO_2$, perfusion, pH, lactic acid, $pCO_2$, etc.). Accordingly, the operator may select a customized configuration of effector units dependent upon particular task and surgical requirements in order to effectuate a multi-view perspective via the operator interface comprised of multiple surgical field views or a combination of simultaneous tool eye view perspectives, field views and monitors.

Any suitable means for communication between the controller 104 and the instrumentalities of the various effector units 209, 601, effector mounts 207, ring structure surgical effector 201, slip disks 208, or other devices disclosed herein, including digital, serial, and optical data relay means, where appropriate, may be used. As can be appreciated by one skilled in the art, any communication protocol appropriate for the relaying of data may be used which effectively communicates instructions and feedback to aspects of the present invention disclosed herein. Such communication methods may be wireless where appropriate.

Returning to FIGS. 1 and 5, an operator 502 of the unit may be provided with an operator interface 107, 503. The operator interface 107, 503 may provide images of the surgical field, either tools eye view or surgical field view, as well as operation parameters associated with surgical implements then in use. The images provided may be enhanced with overlay information, such as information obtained regarding physiologic features obtained via CAT scan, MRI or other imaging devices. Imaging data from such sources may be utilized to provide navigational data to the operator with respect to the control of the effector units and instrumentalities thereof. Such navigational data may be utilized by the controller to automatically slew the desired effector unit 209, 601 and instrument thereof to the relevant position, with or without operator intervention.

Figure 5:
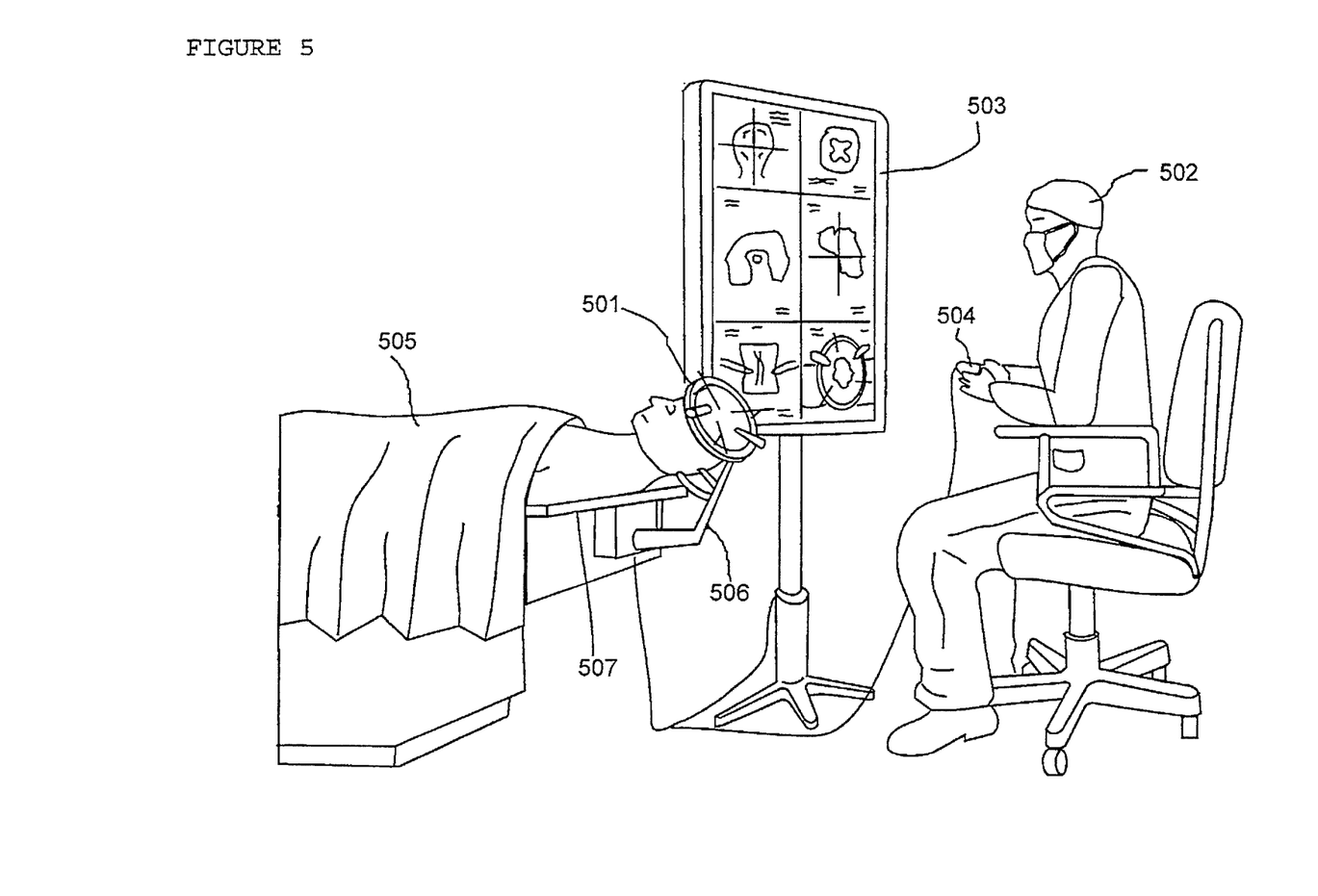
FIG. 5 illustrates a potential configuration a ring form surgical robot according to the present invention, wherein multiple effector units are engaged to the ring form, the operator is controlling the effector units via the operator control interface system, viewing feedback via the operator interface, and the patient is subject to a supporting mechanism.

The images provided by the sensing and imaging instrumentalities of a single or multiple effector units 209, 601 may be displayed via the operator interface 107, 503, or, alternatively, may be combined with imaging data, historical data, or other instructive data from non-related sources to provide a composite display of data pertinent to the operator and the particular task. Such data may be further combined, where applicable, to display a three-dimensional representation of the surgical field, the target surgical area, or other relevant subject. A computer 108, 503 having graphics processing capabilities may be utilized to display the selected data and/or correlate relevant images for real-time three-dimensional modeling and/or the display of raw or processed three-dimensional imaging provided directly via a sensor.

An operator 502 of the unit may further be provided with an operator interface control system 106, 504 by which to manipulate the effector units. To operate on a patient 505, the operator 502 manipulates or otherwise interacts with the operator interface controls 106, 504. These manipulations and interactions are sensed and used to generate corresponding control signals, which are transmitted to the effector units 209, 601 by way of the controller unit 104 for controlling the instrumentalities configured thereupon. The operator interface controls 106, 504 may utilize touch or tactile sensors in order to measure the pressure or force exerted by the user to the interface. Additionally, the operator 502 may receive haptic feedback from the user interface controls 106, 504 correlating to the pressure, force or other sensitivities exerted upon the instrumentalities of the effector units. Further information about such haptic, touch, and tactile control mechanisms can be found in co-pending patent application Ser. Nos. 11/255,899, filed Oct. 20, 2005 and U.S. Pat. No. 7,198,630, issued Apr. 3, 2007.

Computer software may be implemented in order to effectuate the correlation of the multiple data sources contemplated by the present invention. Such software may be extensible to include additional functionality and device support, as well as be capable of mining external data sources for relevant data pertinent to the operation of the instrumentalities disclosed herein; navigation of the effector mounts about the surgical field; internet access; tele-consultation of patients and others in and out of the medical community; tele-mentoring of students and others in and out of the medical community; external database sources containing relevant data sets; provide recording and playback functionality for on-site and off-site review, in both on-demand and archival formats; capable of streaming live-video from the instrumentalities and surgical field to other locations; and support for wired and wireless connectivity. The present invention may further include an uninterruptible power supply or backup power system for the purposes of redundancy and disaster recovery.

As shown in FIG. 5, the ring form 501 may be mounted to an operation table 507 via a ring mounting hardware 506. The ring mounting hardware 506 provides a means to stabilize the ring form 501 in space, as well as stabilize and support the patient's head, where the selected application is neurosurgery, relative to the ring form. Although not illustrated, the ring mounting hardware 506 may further provide for a means of stabilizing the patient 505 on the operating table 507. The ring mounting hardware 506 may further provide a housing or management system through which the data and power connectors are unobtrusively channeled away from the ring form to their respective receptacles.

FIG. 6 illustrates a simplified ring form 601, in which surgical implements may be fixedly attached to the outer ring form structure 601, i.e., once placed, they remain in that position with respect to the ring during a surgical procedure. The ring 601 may include a rail 604 for engaging an effector unit 602, either directly or through an effector mount 603. The ring 601 may additionally be provided with an electrical circuit (not shown) to allow electrical communication between surgical implements and the ring form 601. The surgical implements which may be attached to the ring form 601 may include lights, imaging devices such as cameras, including three dimensional cameras, retractor units, or effector units (not shown.)

The ring form 601 may additionally have structure allowing the ring form 601 to be structurally connected, either directly or indirectly, to a patient (not shown), such that the position of the ring form 601 remains fixed with respect to the patient during a procedure. The structure for structurally connecting the ring form to a patient may include legs 605 extending from the ring form 601, which may be mechanically connected to mounts fixed to the patient, or to an operating table to which the patient has been fixed.

Figure 7:
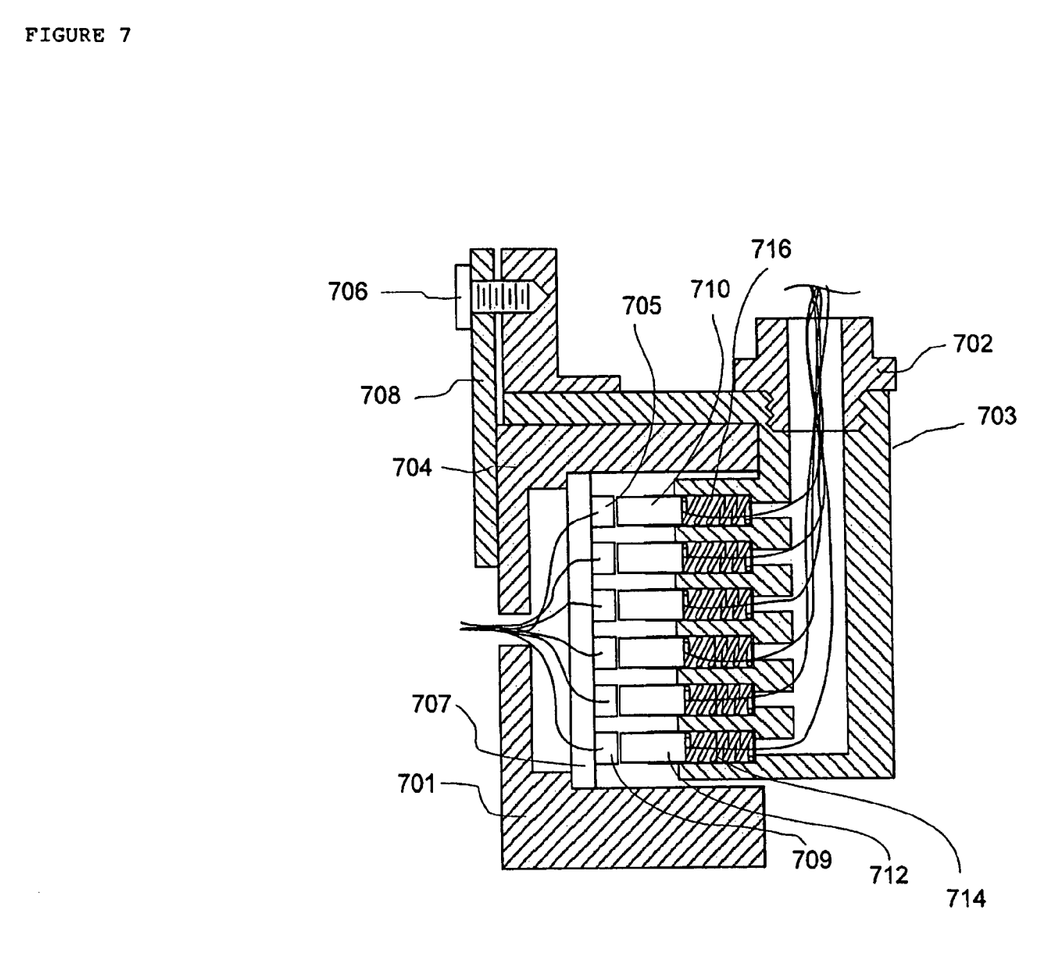
FIG. 7 illustrates the simplified ring form in cross section.

As shown in FIG. 7, the outer ring form structure 701 may include a rail portion 704 which restrains motion of an effector mount 703 attached to the outer ring form 701. The rail 704 may simply be a feature which engages the ring form 701, such that retaining structure holds the effector mount 703 in a fixed position with respect to the ring form 701. This may be accomplished by a back plate 708 connected to the effector mount 603 via a thumb screw 706, such that tightening of the thumb screw 706 tightens the effector mount 703 against the ring structure 701.

The outer ring structure 701 may be provided with a slip ring structure 710, comprising one or more electrical traces 712 extending around the ring form 701, which may be engaged by electrical contacts 714 on a surgical implement or effector mount 703. The contacts 714 may be biased into contact with the electrical traces 712 via a spring loading 716, with the electrical paths further formed by wires extending to a surgical implement (not shown.)

The electrical paths may include connections designated to provide power to a surgical implement. Other contacts may be provided such that a plurality of contacts form a signal bus to allow digital data to be transmitted across the wires. Alternately, specific electrical paths may be designated for transmitting video signals, or control signals for specific surgical implements.

The present system may additionally include fiber-optic communications paths, utilizing fiber-optic slip rings, to increase the amount of data which may be transmitted from a surgical implement, such as an ultrasound transducer, to a controller, or such as to provide a light signal from a remote signal generator to a surgical implement comprising a lens for focusing such light to be applied to tissue of a patient for therapeutic purposes.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention can involve components having different characteristics as long as the principles of the invention are followed.

What is claimed is:

1. A portable powered surgical platform comprising a surgical ring form structurally connectable directly or indirectly to a surgical patient such that the position of the ring form remains fixed with respect to the patient during a surgical procedure, said ring form having a periphery and an opening within the periphery to access a surgical field on the patient, the ring form including a plurality of slip rings extending around and disposed within the periphery of the ring form for permitting communication with a surgical effector unit mounted on the ring form, the plurality of slip rings providing a plurality of electrical paths in an electrical circuit allowing the surgical effector unit to make continuous communication with the plurality of electrical paths in the slip rings as the surgical effector unit is movably mounted at different positions around the ring form, the surgical effector unit being electrically communicable through the plurality of slip rings with a remote controller connected to the ring form.

2. The portable powered surgical platform of claim 1 wherein said ring form includes a rail to which the surgical effector unit may be removably mounted, the rail and continuous electrical contact with the slip rings allowing controlled motion of the surgical effector unit along the rail around the ring form in response to communication with a remote controller connected to the ring form.

3. The portable powered surgical platform of claim 1 wherein said ring form includes a rail around the periphery of the ring form and an effector mount slideable on the rail to which the surgical effector unit may be removably mounted, the rail guiding motion of the effector mount around the ring form, the rail and continuous electrical contact with the slip rings allowing controlled motion of the surgical effector unit on the effector mount along the rail around the ring form in response to communication with a remote controller connected to the ring form.

4. The portable powered surgical platform of claim 1 wherein the plurality of slip rings permit electrical contact with a surgical effector unit mounted on the ring form.

5. The portable powered surgical platform of claim 1 wherein the plurality of slip rings are disposed within the periphery of the ring form, and further including a separable cover over the slip rings adapted to reduce interference with objects in the surgical field and reduce amount of extraneous matter which can enter the ring form.

6. The portable powered surgical platform of claim 1 further including a position sensor determining the position of the surgical effector unit with respect to the ring form.

7. The portable powered surgical platform of claim 1 wherein the plurality of electrical paths in the slip rings provide power to the surgical effector unit as the surgical effector unit is movably mounted at different positions around the ring form.

8. The portable powered surgical platform of claim 1 wherein the plurality of electrical paths in the slip rings provide data communication between the ring form and the surgical effector unit as the surgical effector unit is movably mounted at different positions around the ring form.

9. The portable powered surgical platform of claim 1 wherein the plurality of electrical paths in the slip rings transmit control signals from the ring form to the surgical effector unit as the surgical effector unit is movably mounted at different positions around the ring form.

10. The portable powered surgical platform of claim 1 wherein the plurality of electrical paths in the slip rings transmit data signals from the surgical effector unit to the ring form as the surgical effector unit is movably mounted at different positions around the ring form.

11. The portable powered surgical platform of claim 1 wherein the plurality of electrical paths in the slip rings transmit video signals from the surgical effector unit to the ring form as the surgical effector unit is movably mounted at different positions around the ring form.

12. The portable powered surgical platform of claim 1 wherein shape of the ring form is selected from the group consisting of circular, oval and rectangular.

13. The portable powered surgical platform of claim 1 further including a remote controller connected to the ring form, the plurality of electrical paths forming a signal bus for allowing communication between the remote controller and a plurality of surgical effector units movably mounted at different positions around the ring form.

14. The portable powered surgical platform of claim 1 further including a plurality of effector units mounted on the ring form, the plurality of slip rings providing a plurality of electrical paths allowing the surgical effector units to make continuous communication with the plurality of electrical paths in the slip rings as the surgical effector units are movably mounted at different positions around the ring form, the surgical effector units being electrically communicable through the plurality of slip rings with a remote controller connected to the ring form.

15. The portable powered surgical platform of claim 1 wherein the surgical effector unit is selected from the group consisting of lasers, ultrasound devices, lights and imaging devices.

16. A portable powered surgical platform comprising:
a surgical ring form having a periphery and an opening within the periphery to access a surgical field on the patient,
a structural connector extending from the ring form for fixedly positioning the ring form with respect to a patient during a surgical procedure,
a rail extending around the periphery of the ring form to which a surgical effector unit may be removably mounted, the rail guiding and allowing controlled motion of the surgical effector unit along the rail around the ring form,
a plurality of slip rings extending around and disposed within the periphery of the ring form for permitting spring loaded electrical contact with a surgical effector unit mounted on the ring form, the plurality of slip rings providing a plurality of electrical paths in an electrical circuit allowing the surgical effector unit to make continuous electrical contact with the plurality of electrical paths in the slip rings as the surgical effector unit is moved to different positions around the ring form, the surgical effector unit being electrically communicable through the plurality of slip rings with a remote controller connected to the ring form, and
a separable cover on the ring form over the slip rings adapted to reduce interference with objects in the surgical field and reduce amount of extraneous matter which can enter the ring form.

17. The portable powered surgical platform of claim 16 wherein the plurality of electrical paths in the slip rings provide power to the surgical effector unit as the surgical effector unit is moved.

18. The portable powered surgical platform of claim 16 wherein the plurality of electrical paths in the slip rings provide data communication between the ring form and the surgical effector unit as the surgical effector unit is moved.

19. The portable powered surgical platform of claim 16 further including a position sensor determining the position of the surgical effector unit with respect to the ring form.

* * * * *